United States Patent
McKay (10) Patent No.: US 8,574,302 B2
(45) Date of Patent: Nov. 5, 2013

(54) BONE AUGMENTATION DEVICE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/973,159

(22) Filed: Dec. 20, 2010

(65) Prior Publication Data

US 2012/0156644 A1 Jun. 21, 2012

(51) Int. Cl.
*A61C 8/00* (2006.01)
*A61F 2/02* (2006.01)

(52) U.S. Cl.
USPC .................................. 623/17.17; 433/173

(58) Field of Classification Search
USPC ............... 623/17.17, 17.18, 16.11, 17.19; 433/173, 174; 606/250, 259, 260
See application file for complete search history.

(56) References Cited

U.S. PATENT DOCUMENTS

| | | | |
|---|---|---|---|
| 4,260,383 A * | 4/1981 | Weissman | 433/225 |
| 4,531,916 A | 7/1985 | Scantlebury et al. | |
| 5,417,569 A | 5/1995 | Perisse | |
| 5,470,230 A | 11/1995 | Daftary et al. | |
| 5,509,765 A | 4/1996 | Albin | |
| 5,562,735 A * | 10/1996 | Margulies | 601/61 |
| 5,863,200 A | 1/1999 | Hamada et al. | |
| 5,931,674 A | 8/1999 | Hanosh et al. | |
| 5,951,288 A | 9/1999 | Sawa | |
| 5,954,769 A * | 9/1999 | Rosenlicht | 623/16.11 |
| 5,980,252 A * | 11/1999 | Samchukov et al. | 433/215 |
| 6,227,860 B1 | 5/2001 | Hobo | |
| 6,402,518 B1 | 6/2002 | Ashman | |
| 6,863,530 B2 | 3/2005 | McDevitt | |
| 6,991,461 B2 | 1/2006 | Gittleman | |
| 7,179,088 B2 | 2/2007 | Schulter et al. | |
| 7,559,942 B2 * | 7/2009 | Paul et al. | 606/250 |
| 2005/0159754 A1 | 7/2005 | Odrich | |
| 2006/0247648 A1 * | 11/2006 | Serbousek | 606/90 |
| 2009/0062801 A1 * | 3/2009 | VanMeter, Jr. | 606/79 |
| 2010/0159419 A1 | 6/2010 | Grant | |
| 2010/0215718 A1 | 8/2010 | Swords et al. | |
| 2010/0217331 A1 | 8/2010 | Spagnoli et al. | |

FOREIGN PATENT DOCUMENTS

KR 20030082243 A 10/2003
KR 100545891 B1 1/2006

OTHER PUBLICATIONS

International Search Report and Written Opinion for PCT/US2011/064461, the counterpart application mailed on Jun. 20, 2012.

* cited by examiner

*Primary Examiner* — David Isabella
*Assistant Examiner* — Marcia Hoffman
(74) *Attorney, Agent, or Firm* — Sorell Lenna & Schmidt LLP (57) ABSTRACT

A bone augmentation device includes at least one axial member defining a longitudinal axis and a plurality of transverse members. Each transverse member extends from a first end, removably connected to the at least one axial member to a second end configured for fixation with bone. The transverse members are spaced apart and disposed along the longitudinal axis. The at least one axial member and the transverse members are disposed in a configuration to define a bone graft cavity. Methods of use are also disclosed.

15 Claims, 7 Drawing Sheets

BONE AUGMENTATION DEVICE

TECHNICAL FIELD

The present disclosure generally relates to medical devices for the treatment of bone disorders, for example, periodontal disorders, and more particularly to a bone augmentation device and method including a scaffold configuration of axial and transverse members for augmenting bone, the device being removable with minimal tissue and vascular disruption.

BACKGROUND

Surgical repair and/or reconstruction procedures including those employing implants are widely used in dental and oral surgery for restoration of the jaw anatomy. These procedures are often used to treat bone defects and disorders of the jaw, which may result and/or be caused from periodontal diseases, bone, gum and/or tooth loss, trauma, tumors, infections and other complications. New bone growth is often desired to repair a defect or to build up the jawbone so that sufficient bone exists to embed and retain an implant.

In some cases, a ridge augmentation procedure is employed to add bone to the jaw so that sufficient alveolar bone exists for implant and/or tooth retention. Such procedures can employ a spacing device to facilitate bone growth. After new bone has formed, the devices employed during the augmentation are removed. However, the removal of these devices can cause tissue disruption that undesirably exposes new bone and disrupts vascularity, or can be difficult to remove due to bone overgrowth. This disclosure describes an improvement over these prior art technologies.

SUMMARY OF THE INVENTION

Accordingly, a bone augmentation device and method is provided for treating bone disorders, for example, periodontal disorders. It is contemplated that the bone augmentation device includes a scaffold configuration of axial and transverse members for augmenting bone, the device being removable with minimal tissue disruption. It is further contemplated that the augmentation device is configured to promote bone growth while being easily disassembled such that gingival tissue and vascularity disruption is minimized.

In one particular embodiment, in accordance with the principles of the present disclosure, a bone augmentation device is provided. The bone augmentation device includes at least one axial member defining a longitudinal axis and a plurality of transverse members. Each transverse member extends from a first end, removably connected to the at least one axial member, to a second end configured for fixation with bone. The transverse members are spaced apart and disposed along the longitudinal axis in a transverse orientation relative thereto. The at least one axial member and the transverse members are disposed in a configuration to define a bone graft cavity.

In one embodiment, a jawbone augmentation device is provided. The jawbone augmentation device includes at least one horizontal strut defining a longitudinal axis and a plurality of vertical struts. Each vertical strut extends from a first end defining a closed loop, removably connected to the at least one horizontal strut, to a second end having a linear configuration and being configured for removable fixation with jawbone. The vertical struts are disposed along the longitudinal axis during fixation. The device includes bone graft. The at least one horizontal strut and the vertical struts are disposed in a scaffold configuration to define a cavity configured for disposal of the bone graft. The cavity is disposed between the axial strut and the jawbone.

In one embodiment, a method for augmenting jawbone at a surgical site is provided. The method includes the steps of providing a bone augmentation device, similar to those described herein; providing bone graft configured for disposal within the bone graft cavity; implanting the bone augmentation device and the bone graft with jawbone such that the at least one axial member and the transverse members are disposed in a configuration with the bone graft disposed in the cavity and the second end of each transverse member being fixed with the jawbone; removing the at least one axial member from the surgical site; and removing the transverse members from the jawbone.

BRIEF DESCRIPTION OF THE DRAWINGS

The present disclosure will become more readily apparent from the specific description accompanied by the following drawings, in which.

DETAILED DESCRIPTION OF THE INVENTION

The exemplary embodiments of the bone augmentation device and methods of use disclosed are discussed in terms of medical devices for the treatment of bone disorders, for example, periodontal disorders, and more particularly, in terms of a bone augmentation device and method including a scaffold configuration of axial and traverse members for augmenting bone. The bone augmentation device of the present disclosure is removable with minimal tissue and vascular disruption, and easier to remove than previously known mesh devices. It is envisioned that the bone augmentation device maintains space when attempting to grow new bone either in a defect and/or building up a jawbone in a ridge augmentation procedure. It is further envisioned that the bone augmentation device is employed with a surgical implant to add bone height and/or width to the jaw so that sufficient bone exists to embed and retain an implant while preventing overlying soft tissue and muscle forces from compressing newly forming bone. It is contemplated that the bone augmentation device may be configured as a metal scaffolding device that includes one or a plurality of metal struts, which can interlock with each other to provide mechanical support and be easily dismantled for removal.

It is envisioned that the present disclosure may be employed to treat periodontal disorders such as, for example, peri-implantitis, chronic, aggressive and necrotizing periodontitis, gingivitis and other periodontal diseases. It is contemplated that the present disclosure may be employed with other osteal and bone related applications, including those associated with diagnostics and therapeutics. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Figure 1:
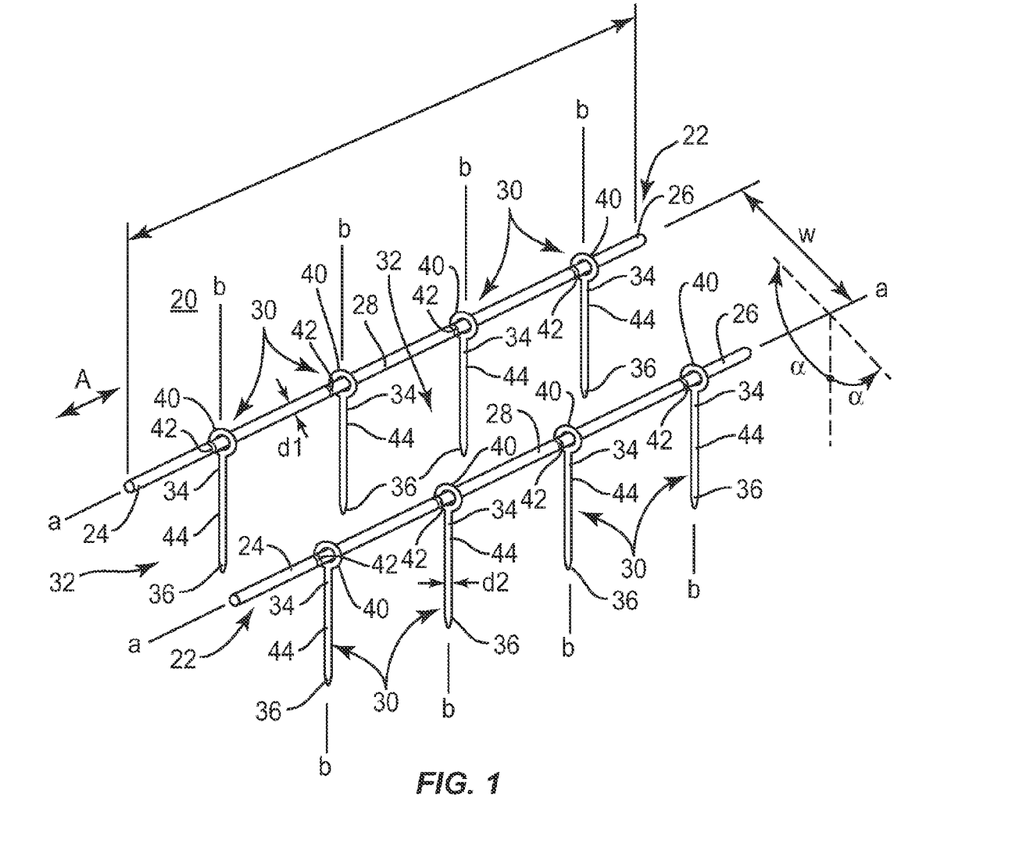
FIG. 1 is a perspective view of one particular embodiment of a bone augmentation device in accordance with the principles of the present disclosure.

The following discussion includes a description of a bone augmentation device and related methods of employing the bone augmentation device in accordance with the principles of the present disclosure. Alternate embodiments are also disclosed. Reference will now be made in detail to the exemplary embodiments of the present disclosure, which are illustrated in the accompanying figures. Turning now to FIG. 1, there is illustrated components of a bone augmentation device 20 in accordance with the principles of the present disclosure.

The components of bone augmentation device 20 are fabricated from materials suitable for medical applications, including metals, polymers, ceramics, biocompatible materials, bone, autograft, allograft and/or their composites, depending on the particular application and/or preference of a medical practitioner. For example, the components of bone augmentation device 20, individually or collectively, can be fabricated from materials such as stainless steel, titanium, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene and epoxy. Various components of bone augmentation device 20 may have material composites, including the above materials, to achieve various desired characteristics such as strength, rigidity, elasticity, compliance, biomechanical performance, durability and radiolucency or imaging preference. The components of bone augmentation device 20 can be made of radiolucent materials such as polymers. Radiomarkers may be included for identification under x-ray, fluoroscopy, CT or other imaging techniques.

Bone augmentation device 20 is configured for treating bone disorders, for example, of the jawbone where new bone growth is desired to repair a defect and/or build up the jawbone for implant retention. The components of bone augmentation device 20 are configured to augment bone and be removed therefrom with minimal disruption to soft tissue and vasculature, as will be described.

Bone augmentation device 20 includes a pair of axial members, such as, for example, horizontal struts 22. Each horizontal strut 22 defines a longitudinal axis a. Horizontal strut 22 extends from a first end 24 to a second end 26, and has an outer surface 28. It is envisioned that all or a portion of horizontal strut 22 may be offset, staggered and/or disposed at an angle from longitudinal axis a.

Outer surface 28 has a smooth or even configuration such that horizontal strut 22 may easily pass through tissue. It is contemplated that tissue includes soft tissue, cartilage and/or bone. It is further contemplated that outer surface 28 may be rough, textured, porous, semi-porous, dimpled and/or polished. Ends 24, 26 are configured for attachment to tissue, which may include fixation, adhesive, instrumentation such as a brace or clip, and/or tissue penetration. It is envisioned that one or both of ends 24, 26 may be attached with tissue for a particular application.

Horizontal strut 22 has a solid, cylindrical configuration and has a thickness, such as, for example, diameter d1. Diameter d1 has a relatively thin or reduced dimension such that horizontal strut 22 may easily pass through tissue. It is envisioned that diameter d1 may be in a range of approximately 1 to 3 millimeters (mm). It is further envisioned that the cross-sectional geometry of horizontal strut 22 may have various configurations, such as, for example, round, oval, oblong, triangular, polygonal having planar or arcuate sides, irregular, uniform, non-uniform, consistent or variable, and/or all or a portion of strut 22 may be porous, perforated, tubular or articulate.

Horizontal strut 22 extends in an axial configuration to support transverse members, such as, for example, vertical struts 30 for treating and conforming to a selected portion of a jawbone at a surgical site according to the requirements of the jaw anatomy and/or a particular application. It is envisioned that horizontal strut 22 may extend in various orientations such as arcuate, undulating, orthogonal, stepped, staggered and/or intermittent with spaced apart ends.

A pair of horizontal struts 22 are disposed in a parallel orientation and are spaced apart in a configuration to define a bone graft cavity 32 with vertical struts 30. It is contemplated that bone augmentation device 20 may include one or a plurality of horizontal struts 22. It is further contemplated that horizontal struts 22 may be disposed in a non-parallel relationship such as angularly offset, converging, diverging, and/or may be monolithically formed or integrally attached. It is envisioned that all or a portion of horizontal strut 22 may be flexible or plastically deformable such that struts 22 are adjustable or can be modified to conform to a selected portion of jawbone for a particular surgical application. It is further envisioned that struts 22 may be formed from a rigid or semi-rigid material to increase strength of bone augmentation device 20 and/or the integrity of bone graft cavity 32.

Vertical struts 30 define a transverse axis b, relative to longitudinal axis a. It is envisioned that all or a portion of vertical strut 30 may be offset, staggered and/or disposed at an angle from longitudinal axis b. It is further envisioned that axis b may be transverse to axis a and disposed at an orientation in a plurality of planes about strut 22 including for example, perpendicular, acute, obtuse, and/or in a range between 0 and 360 degrees, according to the requirements of a particular application.

Vertical strut 30 extends from a first end 34 to a second end 36. First ends 34 of struts 30 are removably connected to horizontal struts 22 to define bone graft cavity 32. First end 34 defines a closed loop, such as, for example, a ring 40 that interlocks with a groove 42 defined in outer surface 28 of horizontal strut 22. Ring 40 is disposed with groove 42 for removable fixation with horizontal strut 22 along longitudinal axis a. It is envisioned that vertical strut 30 may be detachably connected with horizontal strut 22 via clips, hooks, rings, female/male mating parts, snaps, spring bias and/or pressure fit. It is further envisioned that ring 40 may be sized and/or include an insert for a friction engagement with outer surface 28 to fix the orientation of vertical strut 30 relative to horizontal strut 22.

Vertical strut 30 includes an outer surface 44, which has a smooth or even configuration such that vertical strut 30 may easily pass through tissue. It is contemplated that outer surface 44 may be rough, textured, porous, semi-porous, dimpled and/or polished.

Vertical strut 30 has a solid, cylindrical configuration and has a thickness, such as, for example, diameter d2 Diameter d2 has a relatively thin or reduced dimension such that vertical strut 30 may easily pass through tissue. It is envisioned that diameter d2 may be in a range of approximately 1 to 3 mm. It is further envisioned that the cross-sectional geometry of vertical strut 30 may have various configurations, such as, for example, round, oval, oblong, triangular, polygonal having planar or arcuate sides, irregular, uniform, non-uniform, consistent or variable, and/or all or a portion of strut 30 may be porous, perforated, tubular or articulate.

Vertical struts 30 axially extend in a parallel orientation and are spaced apart along horizontal strut 22. Vertical struts 30 extend in a transverse orientation relative to longitudinal axis a to define bone graft cavity 32 for treating and conforming to a selected portion of a jawbone at a surgical site according to the requirements of the jaw anatomy and/or a particular application. It is envisioned that vertical strut 30 may extend in various orientations such as arcuate, undulating, orthogonal, stepped, staggered and/or intermittent with spaced apart ends.

It is contemplated that bone augmentation device 20 may include one or a plurality of vertical struts 30. It is further contemplated that vertical struts 30 may be disposed in a non-parallel relationship such as angularly offset, converging, diverging, and/or may be monolithically formed or integrally attached. It is envisioned that all or a portion of vertical strut 30 may be flexible or plastically deformable such that struts 30 are adjustable or can be modified to conform to a selected portion of jawbone for a particular surgical application. It is further envisioned that struts 30 may be formed from a rigid or semi-rigid material to increase strength of bone augmentation device 20 and/or the integrity of bone graft cavity 32.

Second ends 36 of vertical struts 30 include a sharpened tip for penetrating tissue and removable fixation with a jawbone. Second end 36 fixes with the jawbone to removably mount bone augmentation device 20 with a selected portion of a jawbone at a surgical site according to the requirements of the jaw anatomy and/or a particular application. Second end 36 penetrates the tissues of the jawbone for removable fixation therewith to define bone graft cavity 32 with struts 22, 30. It is contemplated that second end 36 includes a gripping surface to facilitate fixation with the tissue surfaces including bone. The gripping surface may be knurled, rough, textured, dimpled and/or include ribs, teeth and prongs, and/or may be coated with adhesive. It is further contemplated that second end 36 may have various configurations such as a rod for fixation of tissues, pin, spike, threaded and/or be configured for drilling.

In one embodiment, vertical struts 30 are movable relative to horizontal struts 22 to selectively define the configuration and dimension of bone graft cavity 32. Vertical struts 30 are selectively movable along horizontal strut 22, in the direction shown by arrows A in FIG. 1, such that a dimension such as, for example, a length l of bone graft cavity 32 is defined. Horizontal struts 22 are selectively movable with regard to the distance struts 22 are spaced apart, and vertical struts 30 are selectively movable in any one or more of multiple directions (two of which are shown in FIG. 1) through an angle V, such that a dimension, such as, for example, a width w and the cross sectional configuration of bone graft cavity 32 is defined. It is envisioned that struts 22, 30 are selectively movable to define various dimensions of bone graft cavity 32 such as, for example, volume, perimeter and/or surface area to conform to a selected portion of a jawbone and/or for the requirements of a particular application. It is contemplated cavity 32 may extend beyond the boundaries of struts 22, 30 and that various dimensions and configurations of the surgical site may define length l and width w of cavity 32, such as, for example, cavity C discussed below.

Vertical struts 30 are oriented with horizontal struts 22, as described above, to form a scaffold configuration that defines bone graft cavity 32. The scaffold configuration of bone graft cavity 32 can be selectively dimensioned and configured, as discussed, according to the particular surgical application. It is envisioned that the scaffold configuration of bone augmentation device 20 maintains space between new forming bone and tissues of a jaw. Bone graft cavity 32 is disposed between horizontal struts 22 and a selected portion of a jawbone at a surgical site. It is contemplated that bone graft and/or other materials disposed within bone graft cavity 32 may extend beyond cavity 32 and/or the perimeter or boundary established by horizontal struts 22 and/or vertical struts 30.

Bone graft cavity 32 is configured for disposal of and includes bone growth promoting material, such as, for example, bone graft 46 (FIG. 6) and/or other materials adjacent a jaw of a patient, which includes bone, cartilage or other tissues of the upper and lower jaw, gingiva, mandible and/or maxilla. It is envisioned that bone graft 46 is a particulate material, which may include an osteoconductive material such as hydroxyapatite and/or osteoinductive agent such as a bone morphogenic protein to enhance bone growth.

It is contemplated that bone graft 46 may include therapeutic polynucleotides or polypeptides, which can be packed or otherwise disposed in bone graft cavity 32. It is further contemplated that bone graft 46 may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within a patient. Suitable biologically active agents include, for example, bone morphogenic protein (BMP), Growth and Differentiation Factors proteins (GDF) and cytokines.

In one embodiment, horizontal struts 22 and/or vertical struts 30 are fabricated from a resorbable material. It is contemplated that horizontal struts 22 and/or vertical struts 30 are fabricated from a biodegradeable material that resorbs over time in vivo. Examples of such include, but are not limited to, polyglycolide, polylactide, polycaprolactone, poly(ethylene glycol), polyurethanes, polyfumarates, polyacrylamides, collagen, silk, polyamines, polysaccharides, tissue or tissue products, and copolymers and blends thereof. It is further contemplated that struts 22, 30 can be adjusted and/or trimmed to the configuration and dimension requirements of a particular application.

In one embodiment, a plurality of bone augmentation devices 20 of various configurations and dimensions may be packaged as a system or kit that includes bone graft material 46. In such an embodiment, the kit may include one or a plurality of dental prosthetics, implants, abutments and other materials for treatment.

In one embodiment, biologically active agents may be coated onto the exterior of one or all of the components of bone augmentation device 20 and/or applied thereto for gradual release such as by blending in a bioresorbable polymer that releases the biologically active agent or agents in an appropriate time dependent fashion as the polymer degrades within a patient. Suitable biologically active agents include, for example, bone morphogenic protein (BMP) and cytokines.

One or all of the components of bone augmentation device 20, including bone graft 46, may include one or a plurality of agents that can be configured as drug depots with medication for pain and may include antibiotics and/or therapeutics. It is envisioned that the agents may contain active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, am inoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

Referring to FIGS. 2-9, in assembly, operation and use, bone augmentation device 20 is employed with a surgical procedure for treating periodontal disorders in a surgical repair and/or reconstruction procedure. For example, bone augmentation device 20 can be employed to repair a defect and/or build up bone height and/or width of jawbone in a ridge augmentation procedure. Such augmentation can be used to provide sufficient bone for embedding and retaining an implant. Bone augmentation device 20 prevents overlying soft tissue and muscle from compressing new forming bone. Bone augmentation device 20 may also be employed with other surgical procedures for treatment of other periodontal diseases and/or bone disorders of other portions of a patient's anatomy.

Figure 2:
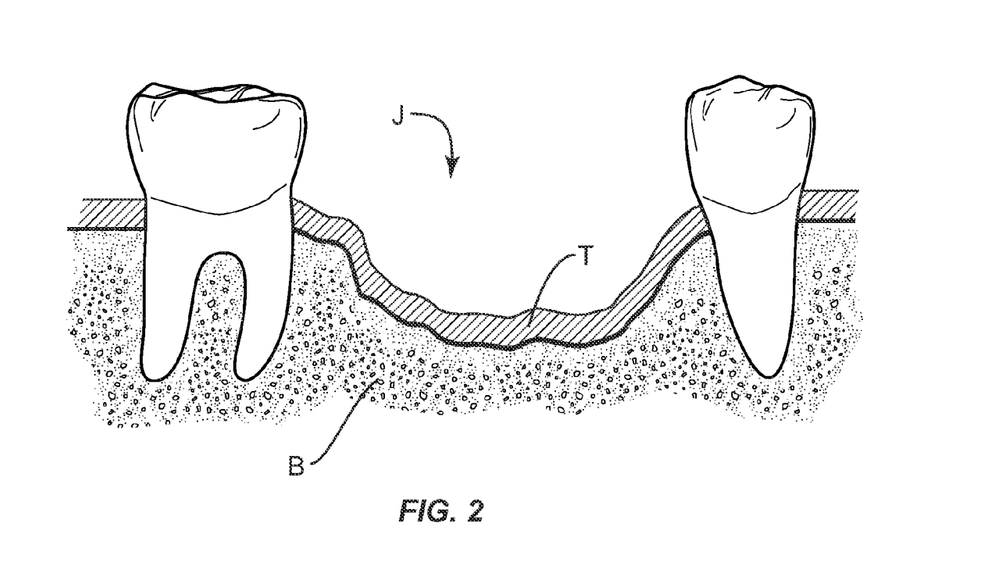
FIG. 2 is a side cutaway view in cross section of a jawbone.
Figure 3:
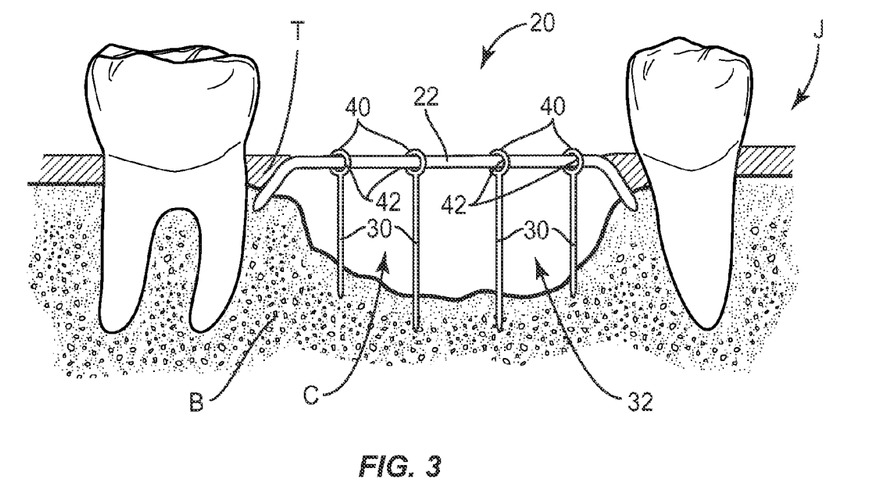
FIG. 3 is a side cutaway view in part cross section of the bone augmentation device shown in FIG. 1 and the jawbone shown in FIG. 2.
Figure 4:
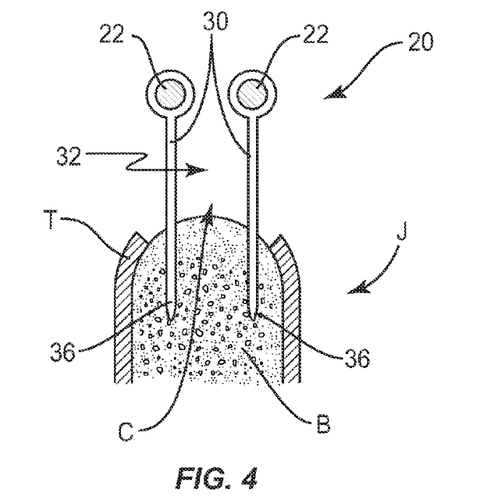
FIG. 4 is an plan view in part cross section of the bone augmentation device and the jawbone shown in FIG. 3.

In use, to treat a section of a jaw J at a surgical site, as shown in FIG. 2, a medical practitioner obtains access to the surgical site including jaw J in any appropriate manner. Gingival soft tissue T is retracted to expose bone B suffering from defect and/or disorder including bone and/or tooth loss, as shown in FIGS. 3 and 4. A cavity C of bone B is mechanically debrided with an instrument (not shown) to remove infection and/or defect including granulation, soft tissue and bone matter. The surfaces of jaw J at the surgical site are cleaned.

Bone augmentation device 20 is provided for mounting with bone B adjacent cavity C to add bone height and width to jaw J. Vertical struts 30 are removably connected with horizontal struts 22 such that rings 40 are disposed within grooves 42, as discussed above. Struts 22, 30 are positioned in alignment with cavity C for fixation with the tissues of jaw J.

Figure 5:
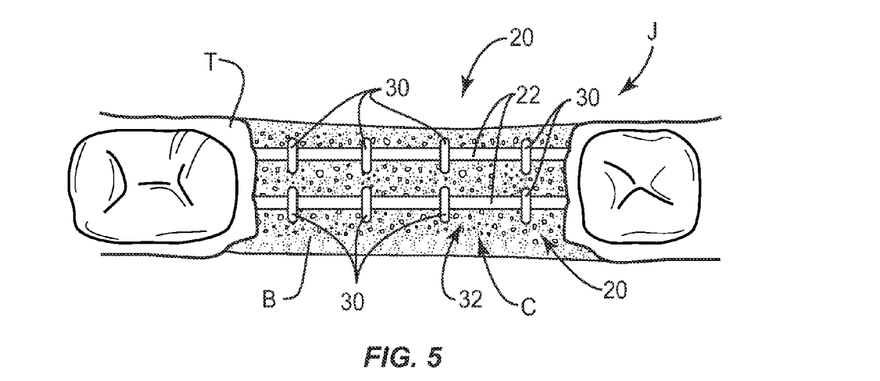
FIG. 5 is a top cutaway view of the bone augmentation device and the jawbone shown in FIG. 3.

Struts 22, 30 are selectively adjusted to define bone graft cavity 32, as discussed above, for the selected configuration and dimension of jaw J to conform to cavity C for treatment thereof. The sharpened tips of second ends 36 are driven to penetrate bone B adjacent cavity C for mounting of bone augmentation device 20 with jaw J in the desired configuration and dimension of bone graft cavity 32, as shown in FIGS. 3-5. Ends 24, 26 of horizontal struts 22 are disposed to attach with bone B adjacent cavity C for mounting of bone augmentation device 20 with jaw J in the desired configuration and dimension of bone graft cavity 32. As shown in FIG. 3, each end 24, 26 is bent or curved with respect to axis a (FIG. 1), and driven to penetrate the surface of bone B to removably fix struts 22 with jaw J. Ends 24, 26, 36 fix with bone B to removably mount bone augmentation device 20 with a selected portion of jaw J at a surgical site according to the requirements of jaw anatomy and/or a particular application.

It is contemplated that ends 24, 26 may be arcuately formed, or alternatively elastically or plastically deformable by a medical practitioner in the process of device implantation. It is further contemplated that ends 24, 26 may include a sharpened tip for penetrating tissue and removable fixation with tissue. It is envisioned that ends 24, 26, 36 may be secured with bone B via adhesive, and/or instrumentation such as clips or braces, and may or may not penetrate bone B. It is further envisioned that strut 22 may not include arcuate ends 24, 26, and that ends 24, 26 have a linear configuration for attachment with bone B, as described herein. As such, each end 24, 26 of horizontal strut 22 may be substantially coaxial or parallel with axis a (FIG. 1), including embodiments of augmentation device 20 in which horizontal strut 22 is and/or remains entirely linear in configuration.

Each end 24, 26 may include a gripping surface to facilitate fixation with tissue. The gripping surface may be knurled, rough, textured, dimpled, and/or include ribs, teeth and prongs, and/or may be coated with adhesive. It is contemplated that ends 24, 26 may have various configurations for fixation with tissue such as a rod, pin, spike, threaded and/or may be configured for drilling and/or hammering. It is further contemplated that one or both ends 24, 26 of horizontal struts 22 may be disposed to attach with, terminate in and/or for unrestricted movement within gingival tissue T.

Figure 6:
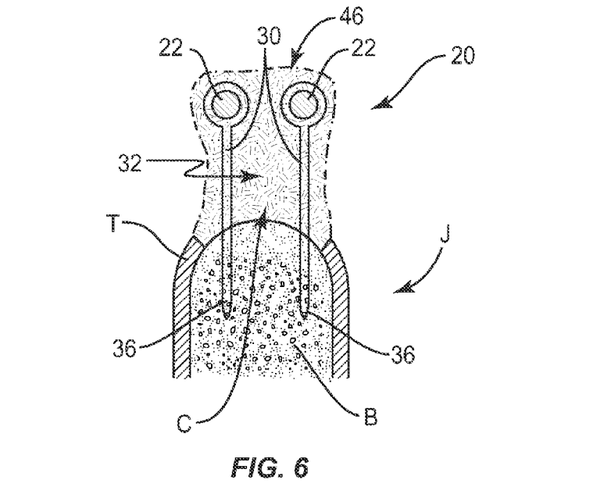
FIG. 6 is a plan view in part cross section of the bone augmentation device and the jawbone shown in FIG. 3 including bone graft.
Figure 7:
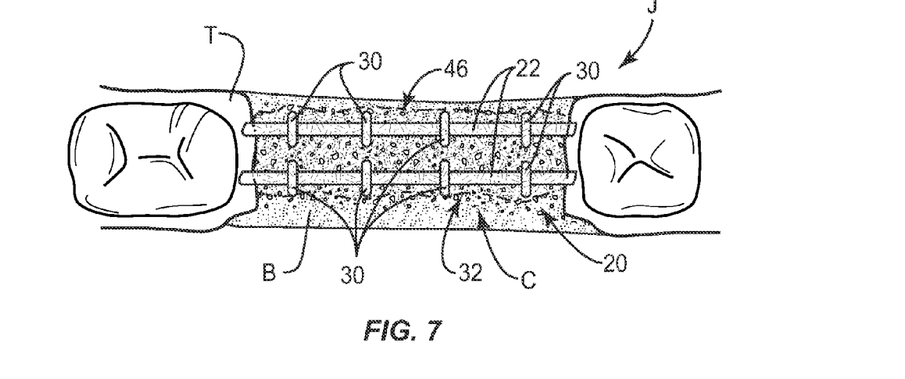
FIG. 7 is a top cutaway view of the bone augmentation device and the jawbone shown in FIG. 6.
Figure 8:
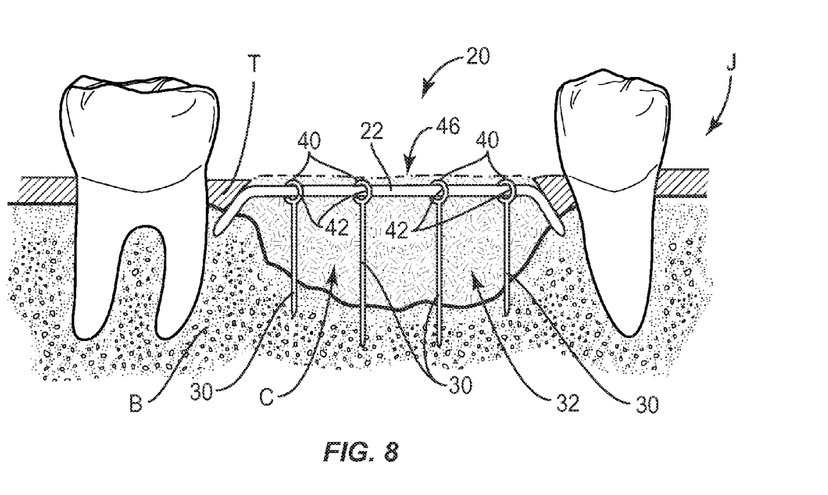
FIG. 8 is a side cutaway view in part cross section of the bone augmentation device and the jawbone shown in FIG. 6.

Referring to FIGS. 6-8, bone augmentation device 20 includes bone graft 46, described above, which is provided and injected within the scaffold configuration of bone graft cavity 32 for treatment of jaw J. Bone graft 46 is employed to promote bone growth to add bone height/width for dental implant retention. It is contemplated that a sufficient amount of bone graft 46 is injected to occupy bone graft cavity 32. It is further contemplated that additional bone graft and/or other material may be provided and/or coated with the components of bone augmentation device 20. In one embodiment, bone graft 46 is installed with struts 22, 30 in a desired configuration and dimension of bone graft cavity 32 prior to mounting of bone augmentation device 20 with the tissues of jaw J.

Figure 9:
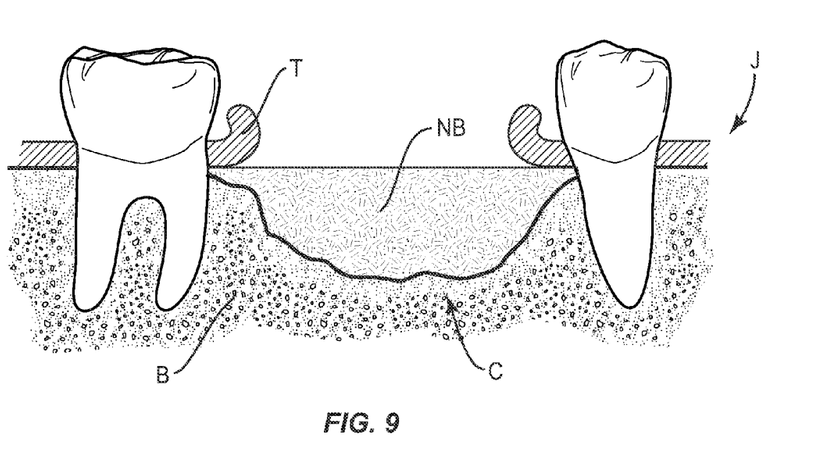
FIG. 9 is a side cutaway view in part cross section of the jawbone shown in FIG. 6.

After new bone growth has formed from bone graft 46 and the tissues of jaw J according to the requirements of a particular application, the surgical site is accessed by a medical practitioner. Horizontal struts 22 are removed from the tissues of jaw J at the surgical site and detachable from vertical struts 30 including detachment of rings 40 from grooves 42. Diameter d1 (FIG. 1) of horizontal strut 22 has a relatively thin or reduced dimension such that horizontal strut 22 may easily pass through the tissues of jaw J including sliding passage through soft tissue and vessels that have grown over newly formed bone NB, as shown in FIG. 9. As such, the configuration of bone augmentation device 20 allows horizontal struts 22 to be slid from the tissues of jaw J with minimal tissue and vascular disruption.

Rings 40 of vertical struts 30 disengage from grooves 42 such that horizontal strut 22 is released from the interlocking fixation with vertical struts 30. Upon removal of horizontal struts 22 and disassembly of the strut components of bone augmentation device 20, vertical struts 30 remain implanted with the tissues of jaw J.

Vertical struts 30 are removed from the tissues of jaw J at the surgical site. Diameter d2 (FIG. 1) of vertical strut 30 has a relatively thin or reduced dimension such that vertical strut 30 may easily pass through the tissues of jaw J including sliding passage through soft tissue and vessels that have grown over newly formed bone NB. As such, the configuration of bone augmentation device 20 allows vertical strut 30 to be slid from the tissues of jaw J with minimal tissue and vascular disruption. Bone augmentation device 20 is removed from the surgical site and bone NB is provided.

Newly formed bone NB is provided to augment the preexisting bone B in cavity C. Gingival tissue T is retracted to expose bone NB, as shown in FIG. 9, which can support, for example, a dental implant. Due to the surgical treatment including the ridge augmentation employing bone augmentation device 20, jaw J includes sufficient bone including bone NB and bone B, for build up of bone height and width of jawbone and/or retention of a dental implant (not shown). It is envisioned that bone augmentation device 20 has provided new bone growth and sufficient stability to jaw J such that subsequent procedures can be performed to attach a prosthetic, dental implant and abutment to jaw J, and/or other treatments or procedures.

In one embodiment, as shown in FIGS. 10-14, bone augmentation device 20 includes a horizontal strut 22, similar to that described above with regard to FIGS. 2-9. Horizontal strut 22 extends in an axial configuration along longitudinal axis a to support transverse members, such as, for example, vertical struts 130 for treating and conforming to a selected portion of a jawbone at a surgical site.

Figure 10:
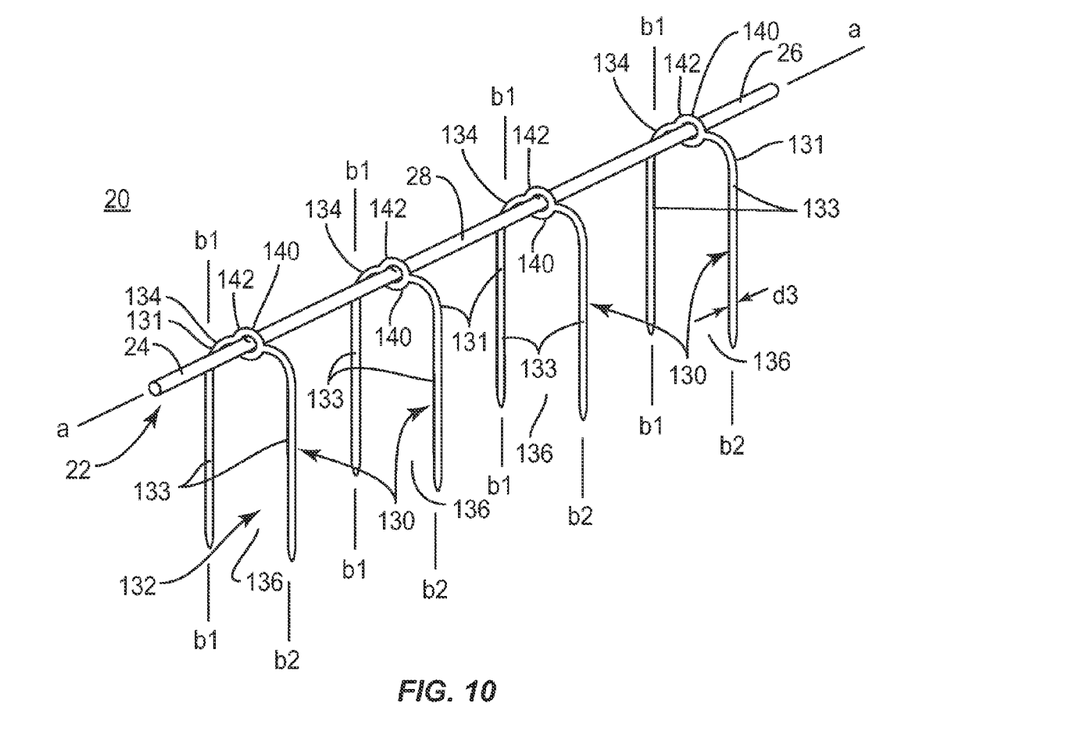
FIG. 10 is a perspective view of one embodiment of the bone augmentation device shown in FIG. 1.

Vertical strut 130 extends from a closed first end 134 to an open second end 136. First ends 134 of struts 130 are removably connected to horizontal struts 22 to define a bone graft cavity 132. First end 134 defines a closed loop, such as, for example, a ring 140 that interlocks with groove 42 defined in outer surface 28 of horizontal strut 22. Ring 140 is disposed with groove 42 for removable fixation with horizontal strut 22.

First end 134 includes arcuate members 131 that extend from ring 140 to second end 136. Second end 136 includes linear members 133, which define transverse axes b1 and b2, respectively, relative to longitudinal axis a. It is envisioned that all or a portion of each of members 131, 133 may be offset, staggered and/or disposed at an angle from axes b1 and b2 It is further envisioned that axes b1 and b2 may be transverse to axis a and disposed at an orientation in a plurality of planes about strut 22 including for example, perpendicular, acute, obtuse, and/or in a range between 0 and 360 degrees, according to the requirements of a particular application.

Members 133 are disposed in a parallel orientation and are spaced apart in a configuration to define a bone graft cavity 132 with horizontal strut 22. It is contemplated that members 133 may be disposed in a non-parallel relationship such as angularly offset, converging, diverging, and/or may be monolithically formed or integrally attached.

Vertical strut 130 includes an outer surface 144, which has a smooth or even configuration such that vertical strut 130 may easily pass through tissue. It is contemplated that outer surface 144 may be rough, textured, porous, semi-porous, dimpled and/or polished. Members 131, 133 of vertical strut 130 have a solid, cylindrical configuration and a thickness, such as, for example, diameter d3. Diameter d3 has a relatively thin or reduced dimension such that members 131, 133 may easily pass through tissue. It is envisioned that diameter d3 may be in a range of approximately 1 to 3 mm.

Vertical struts 130 are disposed in a parallel orientation and are spaced apart along horizontal strut 22. Vertical struts 130 extend in a transverse orientation relative to longitudinal axis a to define bone graft cavity 132 for treating and conforming to a selected portion of a jawbone at a surgical site. It is envisioned that vertical strut 130 may include portions that extend in various orientations such as arcuate, undulating, orthogonal, stepped, staggered and/or intermittent with spaced apart ends.

It is contemplated that bone augmentation device 20 may include one or a plurality of vertical struts 130. It is further contemplated that vertical struts 130 may be disposed in a non-parallel relationship such as angularly offset, converging, diverging, and/or may be monolithically formed or integrally attached. It is envisioned that all or a portion of vertical strut 130 may be flexible or plastically deformable such that struts 130 are adjustable or can be modified to conform to a selected portion of jawbone for a particular surgical application. It is further envisioned that struts 130 may be formed from a rigid or semi-rigid material to increase strength of bone augmentation device 20 and/or the integrity of bone graft cavity 132.

Members 133 of vertical struts 130 include a sharpened tip for penetrating tissue and removable fixation with a jawbone. Member 133 fixes with the jawbone to removably mount bone augmentation device 20 with a selected portion of a jawbone at a surgical site. Member 133 penetrates the tissues of the jawbone for removable fixation therewith to define bone graft cavity 132 with struts 22, 130. It is contemplated that member 133 includes a gripping surface to facilitate fixation with the tissue surfaces including bone, similar to that described above.

Vertical struts 130 are movable relative to horizontal strut 22 to selectively define the configuration and dimension of bone graft cavity 132, similar to that described above. Vertical struts 130 are spaced apart and extend from horizontal strut 22 to form a scaffold configuration that defines bone graft cavity 132. The scaffold configuration of bone graft cavity 132 can be selectively dimensioned and configured, as discussed above. Bone graft cavity 132 is configured for disposal of and includes bone graft 46 (FIGS. 13 and 14), similar to that described above.

Figure 11:
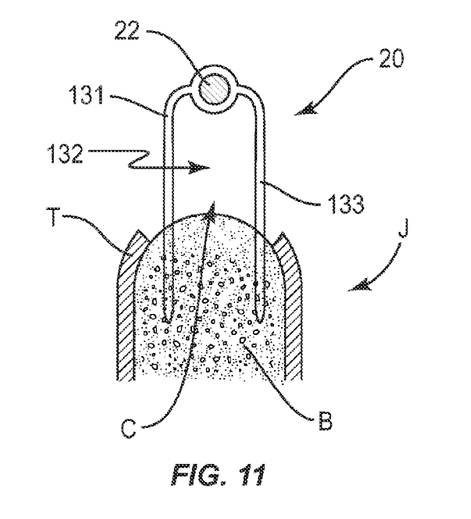
FIG. 11 is a plan view in part cross section of the bone augmentation device shown in FIG. 10 and the jawbone shown in FIG. 2.
Figure 12:
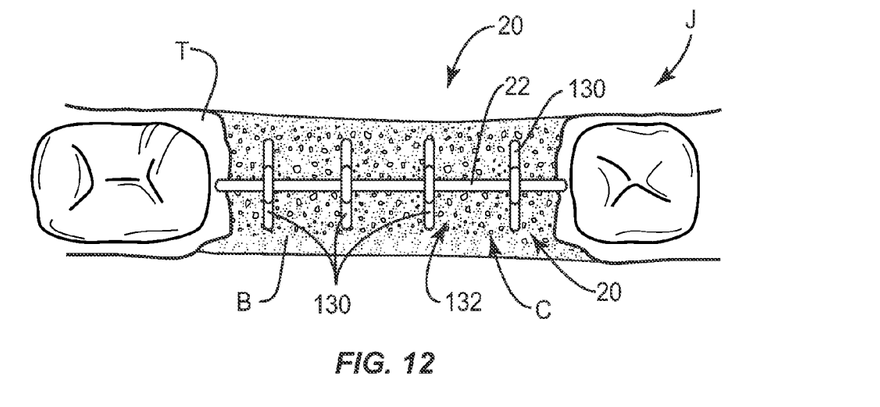
FIG. 12 is a top cutaway view of the bone augmentation device shown in FIG. 10 and the jawbone shown in FIG. 11.

Referring to FIGS. 11-14, in assembly, operation and use, bone augmentation device 20 is employed with a surgical procedure for treating periodontal disorders in a surgical repair and/or reconstruction procedure, similar to that described with regard to FIGS. 2-9. Bone augmentation device 20 is provided for mounting with bone B adjacent cavity C to add bone height and width to jaw J. Vertical struts 130 are detachably connected with horizontal strut 22 such that rings 140 are disposed within grooves 42, as discussed above. Struts 22, 130 are positioned in alignment with cavity C for fixation with the tissues of jaw J, as shown in FIGS. 11 and 12.

Struts 22, 130 are selectively adjusted to define bone graft cavity 132, as discussed above, for the selected configuration and dimension of jaw J to conform to cavity C for treatment thereof. The sharpened tips of members 133 are driven to penetrate bone B adjacent cavity C for mounting of bone augmentation device 20 with jaw J in the desired configuration and dimension of bone graft cavity 132.

Figure 13:
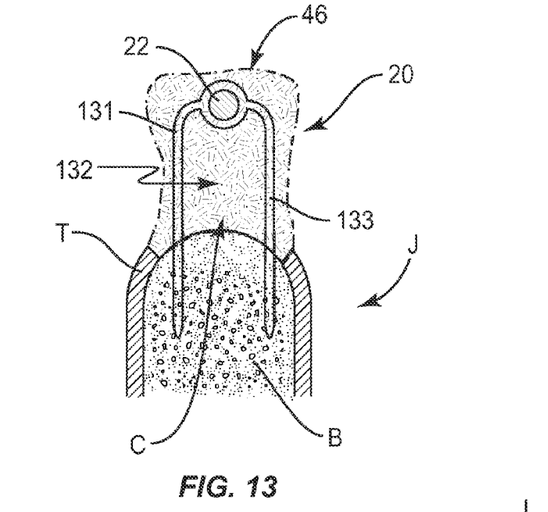
FIG. 13 is a plan view in part cross section of the bone augmentation device and the jawbone shown in FIG. 11 including bone graft.
Figure 14:
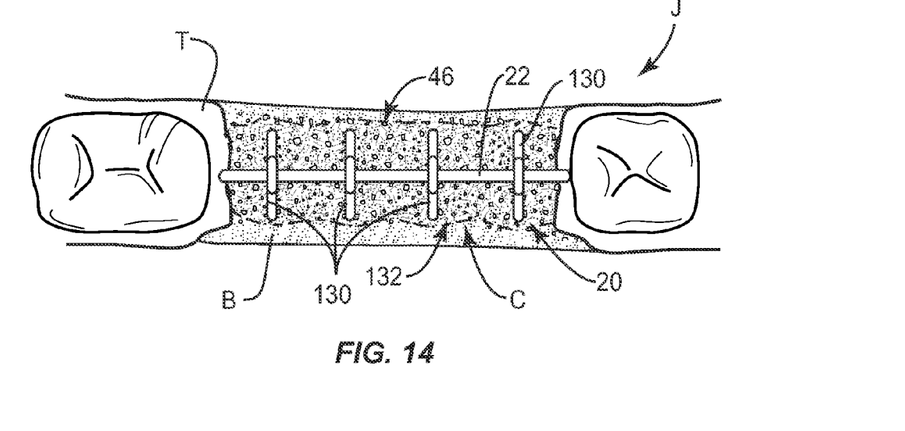
FIG. 14 is a top cutaway view of the bone augmentation device and the jawbone shown in FIG. 13.

Referring to FIGS. 13 and 14, bone augmentation device 20 includes bone graft 46, which is provided and injected within the scaffold configuration of bone graft cavity 132 for treatment of jaw J. Bone graft 46 is employed to promote bone growth to add bone height/width for dental implant retention. After new bone growth has formed, horizontal strut 22 is removed from the tissues of jaw J at the surgical site and detachable from vertical struts 130 including detachment of rings 140 from grooves 42. Diameter d1 (FIG. 1) of horizontal strut 22 allows strut 22 to be slid from the tissues of jaw J with minimal tissue and vascular disruption.

Rings 140 of vertical struts 130 disengage from grooves 42 such that horizontal strut 22 is released from the interlocking fixation with vertical struts 130. Upon removal of horizontal strut 22 and disassembly of the strut components of bone augmentation device 20, vertical struts 130 remain implanted with the tissues of jaw J.

Vertical struts 130 are removed from the tissues of jaw J at the surgical site. Diameter d3 (FIG. 10) of vertical strut 130 has a relatively thin or reduced dimension such that vertical strut 130 may easily pass through the tissues of jaw J including sliding passage through soft tissue and vessels that have grown over the newly formed bone. As such, the configuration of bone augmentation device 20 allows vertical strut 130 to be slid from the tissues of jaw J with minimal tissue and vascular disruption. Bone augmentation device 20 is removed from the surgical site and new bone is provided for the exemplary purposes described above with regard to FIG. 9.

Figure 15:
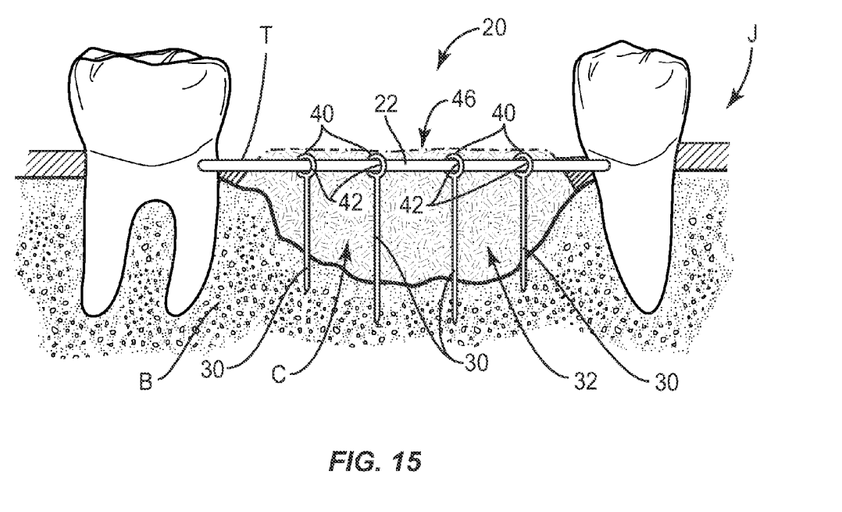
FIG. 15 is a side cutaway view in part cross section of one embodiment of the bone augmentation device shown in FIG. 1.

In one embodiment, as shown in FIG. 15, bone augmentation device 20, similar to that described above with regard to FIGS. 1-9, includes horizontal strut(s) 22 having ends 24, 26 (FIG. 1, also shown in FIG. 10 and applicable to this embodiment). Ends 24, 26 are configured for attachment directly to a surface of teeth of jaw J via adhesive such as a biocompatible glue or other adhesive. One or a plurality of struts 22 may be adhered to the teeth. For example, strut(s) 22 may be attached to the teeth above the gum line, slightly below the gum line and/or within gingival tissue T, adjacent to cavity C. The adhesive interface between ends 24, 26 and the teeth adjacent to cavity C may be temporary, and/or fabricated from a biodegradable material that resorbs over time in vivo, to facilitate removal of bone augmentation device 20 by a medical practitioner after new bone growth has formed from bone graft 46 and the tissues of jaw J. It is envisioned that strut(s) 22 may be adhered to other tissues of jaw J.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone augmentation device for treating periodontal disorders comprising:
    at least one axial member defining a longitudinal axis, the at least one axial member comprising a plurality of grooves that are spaced apart along the longitudinal axis; and
    a plurality of transverse members, each transverse member extending from a first end, removably connected to the at least one axial member, to a second sharpened end configured for fixation with bone, each of the transverse members defining a smooth outer surface configured to pass through tissue, the transverse members each being spaced apart and disposed in one of the grooves along the longitudinal axis in a transverse orientation relative thereto, the first end of each of the transverse members defining a single closed loop configured to receive the at least one axial member and each transverse member is a single piece,
    wherein the at least one axial member and the transverse members are disposed in a configuration to allow a bone graft to be disposed under the axial member, wherein the at least one axial member defines a linear intermediate portion between a first end and a second end, the first and second ends being angled in opposite directions relative to the intermediate portion, the first and second ends each including a pointed tip configured to penetrate tissue.

2. The bone augmentation device of claim 1, wherein the at least one axial member is an elongated strut.

3. The bone augmentation device of claim 1, wherein the at least one axial member includes a plurality of spaced apart axial members.

4. The bone augmentation device of claim 1, wherein the at least one axial member includes a pair of axial members disposed in a parallel orientation.

5. The bone augmentation device of claim 1, wherein each of the transverse members has a linear configuration that extends from the at least one axial member.

6. The bone augmentation device of claim 1, wherein each of the transverse members has an arcuate first end and a linear second end.

7. The bone augmentation device of claim 1, wherein each of the transverse members has a closed first end and an open second end.

8. The bone augmentation device of claim 1, wherein the transverse members are disposed in a parallel orientation during fixation with bone.

9. The bone augmentation device of claim 1, further comprising a bone graft disposed under the axial member, the bone graft comprising at least one therapeutic agent configured to treat the periodontal disorders.

10. A jawbone augmentation device comprising:
at least one horizontal strut defining a longitudinal axis, the at least one horizontal strut comprising a plurality of grooves that are spaced apart along the longitudinal axis;
a plurality of vertical struts, each vertical strut extending from a first end defining a single closed loop, removably connected to the at least one horizontal strut, to a sharpened second end having a linear configuration and being configured for removable fixation with a jawbone, each of the vertical struts defining a smooth outer surface configured to pass through tissue, the vertical struts each being disposed in one of the grooves along the longitudinal axis during fixation and each of the vertical struts being a single piece; and
a bone graft comprising one or more agents configured to augment the jawbone,
wherein the at least one horizontal strut and the vertical struts are disposed in a scaffold configuration, the bone graft being disposed under the horizontal strut, wherein the at least one axial member defines a linear intermediate portion between a first end and a second end, the first and second ends being angled in opposite directions relative to the intermediate portion, the first and second ends each including a pointed tip configured to penetrate tissue.

11. The jawbone augmentation device of claim 10, wherein the at least one horizontal strut includes a plurality of spaced apart horizontal struts.

12. The jawbone augmentation device of claim 10, wherein the at least one horizontal strut includes a pair of horizontal struts disposed in a parallel orientation.

13. The jawbone augmentation device of claim 10, wherein each of the vertical struts has an arcuate first end and a linear second end.

14. The jawbone augmentation device of claim 10, wherein the vertical struts are disposed in a parallel orientation to each other during fixation.

15. The jawbone augmentation device of claim 10, wherein the bone graft is configured to be injected under the horizontal strut.

* * * * *